US00PP18817P2

(12) United States Plant Patent
Blom

(10) Patent No.: US PP18,817 P2
(45) Date of Patent: May 20, 2008

(54) ***ECHINACEA* PLANT NAMED 'PINK SORBET'**

(50) Latin Name: *Echinacea purpurea*
Varietal Denomination: Pink Sorbet

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 18 days.

(21) Appl. No.: 11/527,810

(22) Filed: Sep. 27, 2006

(51) Int. Cl.
*A01H 5/00* (2006.01)

(52) U.S. Cl. ..... Plt./263
(58) Field of Classification Search ..... Plt./263, Plt./258
See application file for complete search history.

(56) References Cited

U.S. PATENT DOCUMENTS

PP13,894 P2 * 6/2003 van Winsen ..... Plt./263

OTHER PUBLICATIONS

UPOV ROM GTITM Computer Database, GTI Jouve Retrieval Software, 2007/01 Citation(s) for 'Pink Sorbet'.*

* cited by examiner

*Primary Examiner*—Wendy Haas
(74) *Attorney, Agent, or Firm*—C. A. Whealy

(57) ABSTRACT

A new and distinct cultivar of *Echinacea* plant named 'Pink Sorbet', characterized by its upright and somewhat outwardly spreading plant habit; moderately vigorous growth habit; freely basal branching habit; and large inflorescences with dark pink-colored ray and disc florets.

2 Drawing Sheets

Botanical designation: *Echinacea purpurea.*
Cultivar denomination: 'Pink Sorbet'.

BACKGROUND OF THE INVENTION

The present invention relates to a new and distinct cultivar of *Echinacea* plant, botanically known as *Echinacea purpurea,* and hereinafter referred to by the name 'Pink Sorbet'.

The new *Echinacea* is a product of a planned breeding program conducted by the Inventor in The Netherlands. The objective of the breeding program is to create new compact *Echinacea* cultivars with unique inflorescence form and attractive ray floret coloration.

The new *Echinacea* originated from a cross-pollination in Bovenkarspel, The Netherlands in July, 2003, of a proprietary selection of *Echinacea purpurea* identified as code number Ec 201-01, not patented, as the female, or seed, parent with a proprietary selection of *Echinacea purpurea* identified as code number Ec 203-01, not patented, as the male, or pollen, parent. The new *Echinacea* was discovered and selected by the Inventor as a single flowering plant from within the progeny of the stated cross-pollination grown in a controlled environment in IJsselstein, The Netherlands.

Asexual reproduction of the new *Echinacea* by micropropagation in The Netherlands since 2004, has shown that the unique features of this new *Echinacea* are stable and reproduced true to type in successive generations.

SUMMARY OF THE INVENTION

The cultivar Pink Sorbet has not been observed under all possible environmental conditions. The phenotype may vary somewhat with variations in environment such as temperature and light intensity, without, however, any variance in genotype.

The following traits have been repeatedly observed and are determined to be the unique characteristics of 'Pink Sorbet'. These characteristics in combination distinguish 'Pink Sorbet' as a new and distinct cultivar of *Echinacea:*

1. Upright and somewhat outwardly spreading plant habit.
2. Moderately vigorous growth habit.
3. Freely basal branching habit.
4. Large inflorescences with dark pink-colored ray and disc florets.

Plants of the new *Echinacea* differ from plants of the female parent selection in the following characteristics:

1. Plants of the new *Echinacea* are more compact than plants of the female parent selection.
2. Plants of the new *Echinacea* have stronger stems than plants of the female parent selection.

Plants of the new *Echinacea* differ from plants of the male parent selection in the following characteristics:

1. Plants of the new *Echinacea* are taller than plants of the male parent selection.
2. Plants of the new *Echinacea* are less freely branching than plants of the male parent selection.

Plants of the new *Echinacea* can be compared to plants of the *Echinacea* cultivar Razzmatazz, disclosed in U.S. Plant Pat. No. 13,894. In side-by-side comparisons conducted in Vleuten, The Netherlands, plants of the new *Echinacea* differed from plants of the cultivar Razzmatazz in the following characteristics:

1. Plants of the new *Echinacea* had stronger stems than plants of the cultivar Razzmatazz.
2. Plants of the new *Echinacea* had larger inflorescences than plants of the cultivar Razzmatazz.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea*.

The photograph on the first sheet comprises a side perspective view of a typical flowering plant of 'Pink Sorbet' grown in a container.

The photograph at the top of the second sheet is a close-up view of a typical inflorescence of 'Pink Sorbet'.

The photograph at the bottom of the second sheet is a close-up view of a typical leaf of 'Pink Sorbet'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Vleuten, The Netherlands during the summer in an outdoor nursery and under conditions and practices which approximate those generally used in commercial *Echinacea* production. During the production of the plants, day temperatures ranged from −5° C. to 35° C. and night temperatures ranged from −8° C. to 20° C. Measurements and numerical values represent averages for typical flowering plants. Plants were about 16 months year old when the photographs and description were taken.

Botanical classification: *Echinacea purpurea* cultivar Pink Sorbet.

Parentage:

*Female parent.*—Proprietary selection of *Echinacea purpurea* identified as code number Ec 201-01, not patented.

*Male parent.*—Proprietary selection of *Echinacea purpurea* identified as code number Ec 203-01, not patented.

Propagation:

*Type.*—By micropropagation.

*Time to initiate roots.*—About one week at 25° C.

*Time to produce a rooted young plant.*—About five weeks at 22° C.

*Root description.*—Fine, fibrous; pale cream white in color.

*Rooting habit.*—Freely branching; moderately dense.

Plant description:

*Plant form/growth habit.*—Upright and somewhat outwardly spreading plant habit; freely basal branching with about eight primary branches developing per plant. Moderately vigorous growth habit.

*Plant height.*—About 79 cm.

*Plant diameter or spread.*—About 48 cm.

*Basal branches.*—Length: About 67.1 cm. Diameter: About 5 mm. Internode length: About 6.9 cm. Aspect: Mostly upright. Strength: Strong. Texture: Pubescent; rough. Color: 144A.

Foliage description:

*Arrangement.*—Alternate, simple.

*Length.*—About 9.8 cm.

*Width.*—About 5 cm.

*Shape.*—Ovate.

*Apex.*—Acute.

*Base.*—Attenuate.

*Margin.*—Irregularly and sparsely serrate.

*Texture, upper and lower surfaces.*—Pubescent; rough.

*Venation pattern.*—Pinnate.

*Color.*—Developing foliage, upper surface: 137A to 137B. Developing foliage, lower surface: 137C. Fully expanded foliage, upper surface: 137A; venation, 144B. Fully expanded foliage, lower surface: 137C; venation, 144B to 144C.

*Petiole length.*—About 7.8 cm.

*Petiole diameter.*—About 2 mm.

*Petiole texture, upper surface.*—Smooth, glabrous.

*Petiole texture, lower surface.*—Sparsely pubescent.

*Petiole color, upper surface.*—144A to 144B.

*Petiole color, lower surface.*—144B.

Inflorescence description:

*Appearance.*—Rotate single inflorescence form with ray and disc florets. Inflorescences positioned above the foliage on strong peduncles and face upright. About two inflorescences develop per lateral branch. Inflorescences not persistent.

*Fragrance.*—Faint, sweet.

*Time to flower.*—Plants flower continuously from late July to late September in The Netherlands.

*Inflorescence longevity.*—Inflorescences maintain good substance for about three weeks on the plant.

*Inflorescence bud.*—Height: About 2 cm. Diameter: About 3.2 cm. Shape: Broadly ovate. Color: Between 144A and N144A.

*Inflorescence size.*—Diameter: About 6 cm. Depth (height): About 6.6 cm. Disc diameter: About 2.9 cm. Receptacle height: About 1.4 cm. Receptacle diameter: About 1.4 cm.

*Ray florets.*—Length: About 3.8 cm. Width: About 9 mm. Shape: Oblanceolate. Apex: Praemorse. Base: Cuneate. Margin: Entire. Texture, upper and lower surfaces: Smooth, glabrous. Number of ray florets per inflorescence: About 15 arranged in a single whorl. Aspect: Drooping. Color: When opening, upper surface: 63B; towards the base, 63A. When opening, lower surface: 185D. Fully opened, upper surface: 63C; towards the base and apex, 63D. With development, 186D tinted with 144C to 144D. Fully opened, lower surface: 186D; towards the base and apex, 144B to 144C. With development, 160B.

*Disc florets.*—Length: About 2.2 cm. Diameter: About 6 mm. Shape: Oblanceolate to tubular, enlarged; apices praemorse. Number of disc florets per inflorescence: About 400. Texture, upper and lower surfaces: Smooth, glabrous. Color: Immature, upper or inner surface: 63A. Immature, lower or outer surface: 63B to 63C. Mature, upper or inner surface: 63B. Mature, lower or outer surface: 63C.

*Receptacle spines.*—Quantity: One per disc floret. Shape: Acicular. Apex: Acute. Base: Attenuate. Texture: Smooth, glabrous. Color: Apex: 25B; at apex, N34A. Mid-section: 143A. Base: 145C to 145D.

*Involucral bracts.*—Quantity per inflorescence: About 54 in about three whorls. Length: About 1.1 cm. Width: About 2.5 mm. Shape: Lanceolate. Apex: Acute. Base: Cuneate. Margin: Entire. Texture, upper surface: Smooth, glabrous. Texture, lower surface: Densely pubescent. Color, upper surface: 143A to 143B. Color, lower surface: 143B to 143C.

*Peduncles.*—Length: About 11.9 cm. Diameter: About 3.5 mm. Strength: Strong. Aspect: Mostly upright. Texture: Pubescent; rough. Color: 144B.

*Reproductive organs.*—Androecium: Quantity per disc floret: Two. Filament length: About 2 mm. Filament color: 165C to 165D. Anther shape: None observed. Gynoecium: Pistil length: About 5 mm. Stigma shape: Cleft; reflexed. Stigma color: 59A. Style length: About 4 mm. Style color: 155A; towards the apex, 60C to 60D. Ovary color: 157D. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind, have been observed to be hardy to USDA Zone 4 and to tolerate high temperatures of about 35° C.

It is claimed:

1. A new and distinct *Echinacea* plant named 'Pink Sorbet' as illustrated and described.

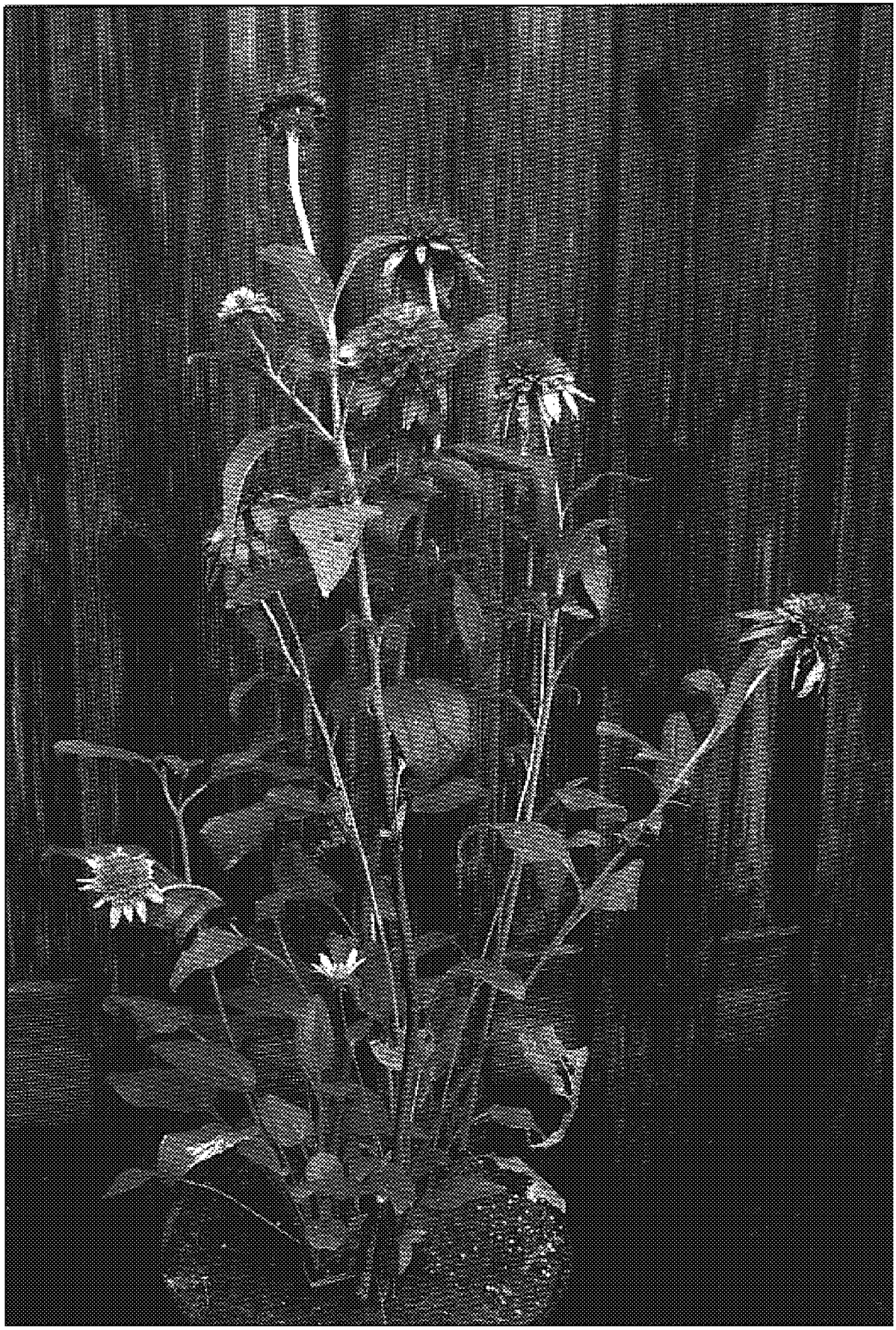

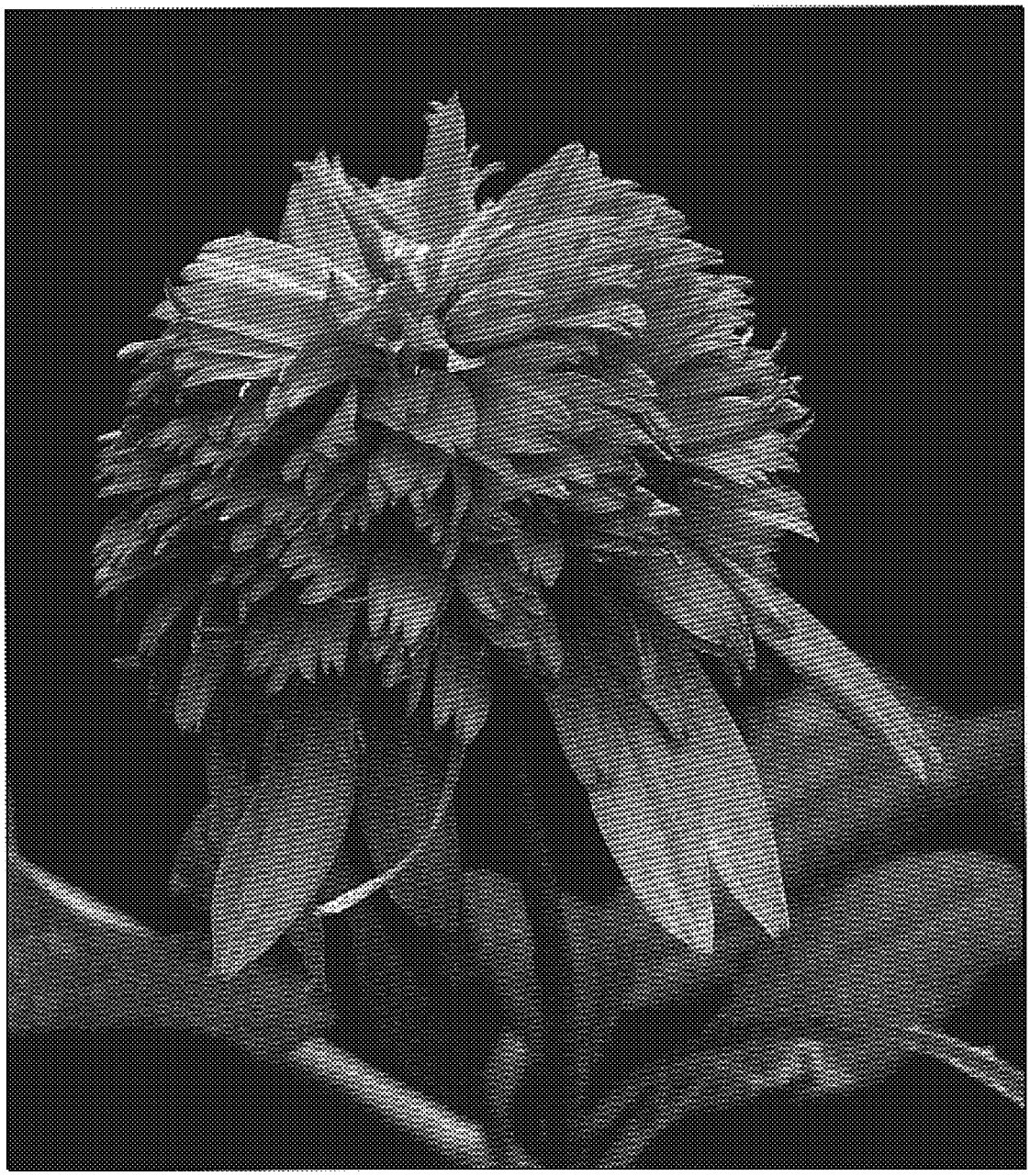
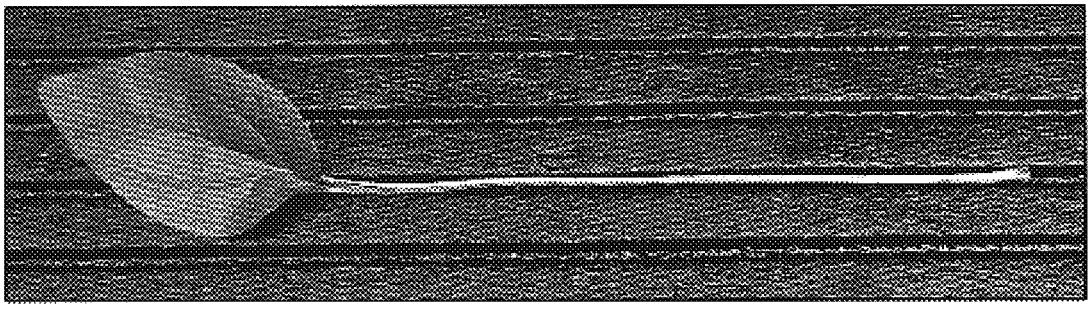

* * * * *